United States Patent [19]

Freed

[11] Patent Number: 4,483,991
[45] Date of Patent: Nov. 20, 1984

[54] HYPOTENSIVE AGENTS
[75] Inventor: Meier E. Freed, Paoli, Pa.
[73] Assignee: American Home Products Corporation, New York, N.Y.
[21] Appl. No.: 458,376
[22] Filed: Jan. 17, 1983
[51] Int. Cl.$^3$ .................. C07D 211/40; C07D 207/08
[52] U.S. Cl. ..................... 546/189; 424/263; 424/274; 546/208; 548/518
[58] Field of Search ............... 546/189, 208; 548/518

[56] References Cited

U.S. PATENT DOCUMENTS

| | | | |
|---|---|---|---|
| 3,051,722 | 8/1962 | Biel | 546/208 X |
| 3,586,678 | 6/1971 | Kühnis et al. | 546/189 X |
| 3,647,804 | 3/1972 | Rynbrandt et al. | 546/208 X |
| 3,804,842 | 4/1974 | Dimming | 546/189 |
| 4,077,951 | 3/1978 | Loffet | 548/518 X |
| 4,374,991 | 2/1983 | Smolanoff | 548/518 X |
| 4,394,504 | 7/1983 | Commons et al. | 544/25 X |

FOREIGN PATENT DOCUMENTS 1249643 10/1971 United Kingdom ............... 546/208

Primary Examiner—Joseph Paul Brust
Attorney, Agent, or Firm—Richard K. Jackson

[57] ABSTRACT

Compounds of the formula:

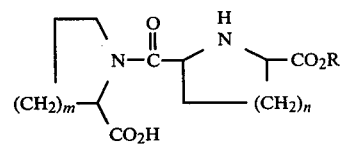

in which
R is alkyl or aralkyl,
m and n are 1 or 2, or a pharmaceutically acceptable salt thereof are antihypertensive agents.

6 Claims, No Drawings

HYPOTENSIVE AGENTS

BRIEF DESCRIPTION OF THE INVENTION

Compounds of the formula:

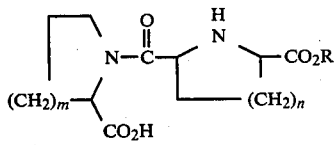

in which
R is alkyl of 1 to 6 carbon atoms or aralkyl of 7 to 9 carbon atoms,
and m and n are independently one of the integers 1 or 2,
or a pharmaceutically acceptable salt thereof are antihypertensive agents.

DETAILED DESCRIPTION OF THE INVENTION

In accordance with this invention there is provided a novel group of pyrrolidine 2,5-dicarboxylic acid derivatives and piperidine 2,6-dicarboxylic acid derivatives which are antihypertensive agents and present the structural formula:

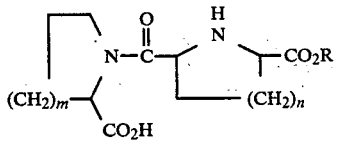

in which
R is alkyl of 1 to 6 carbon atoms or aralkyl of 7 to 9 carbon atoms, and
m and n are independently one of the integers 1 or 2, or a pharmaceutically acceptable salt thereof.

Within the scope of the compound genus depicted supra, are the preferred anti-hypertensive agents comprising those compounds in which R is alkyl of 1 to 4 carbon atoms, such as methyl, ethyl, propyl, isopropyl, butyl, isobutyl and tertiary butyl, m and n are both 1, and the ortho,ortho'-dicarboxylic acid groups are in trans configuration to one another. The pharmaceutically acceptable salts of the compounds of this invention are those conventionally employed such as the sodium, potassium, lithium, ammonium, alkylamine, dialkylamine salts and the like, where the alkyl groups contain from 1 to 6 carbon atoms. The aralkyl groups represented by R embrace benzyl, phenethyl, dimethylbenzyl, and similar groups.

The compounds of this invention are produced by the following reaction scheme:

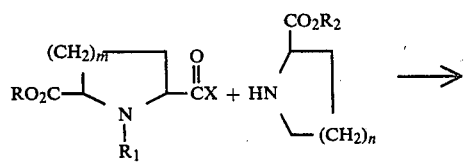

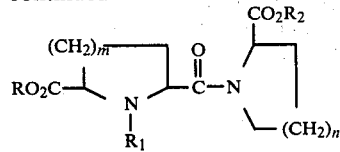

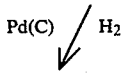

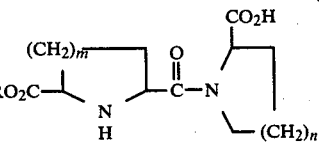

where
R, m and n are defined supra;
X is a halogen;
$R_1$ is an amine protecting group, and
$R_2$ is a carboxyl group;
followed by conversion of the free acid to the desired salt by conventional means such as controlled neutralization in solution or via use of a cation exchange resin.

The carboxyl group protection is accomplished by conversion to an ester or anhydride. The benzyl ester is preferred. The amine protecting group may be tosyl, benzyloxycarbonyl, adamantyloxycarbonyl or tert-butyloxycarbonyl; preferably, the benzyloxycarbonyl group is used.

The ortho,ortho'-dicarboxylic acid halide, alkyl or aralkyl ester reactants are novel compounds. They are produced from the known N-benzyl dicarboxylic diethyl esters by partial saponification and acidification to obtain the N-benzyl, dicarboxylic acid monoethyl ester followed by removal of the N-benzyl group by hydrogenation, N-protection with benzyl chloroformate and conversion of the free acid to an acid halide with $PCl_5$, $POCl_3$, $SOCl_2$, $POBr_3$ or an analogous halogenating agent. Each of these process steps are performed by conventional techniques well known to the chemist.

The anti-hypertensive activity of the compounds of this invention was established with the following scientifically recognized, standard test in which the systolic pressure of male spontaneously hypertensive rats is indirectly measured with a sensor such as the Decker Caudal Plethysmograph. The blood pressure readings are made prior to oral administration of the compound being tested at 1.5 hours after administration.

Following this test procedure, the product of Example 5 which is representative in its activity of the other compounds of this invention, afforded a drop in blood pressure of 21 millimeters mercury at a dose of 25 mg/kg.

For treatment of hypertension, the compounds of this invention must be administered under the guidance of a physician. Unit dosage forms containing from about 1 to 5 grams for single or plural daily administrations are considered appropriate for oral administration.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of provid-

3 ing suitable pharmaceutically acceptable solid or liquid dosage unit forms.

The following examples illustrate the preparation of the anti-hypertensive agents of this invention.

EXAMPLE 1

N-benzyl-2,5-pyrrolidine dicarboxylic acid monoethyl ester

Potassium hydroxide (6.7 g, 0.1 m) in ethanol (180 ml) was slowly added to a solution of trans-1-benzyl-2,5-pyrrolidine dicarboxylic acid diethyl ester in ethanol (300 ml) at room temperature. This was stirred for 36 hours. The solvent was evaporated off and the residue dissolved in water. The pH of the solution was adjusted to 8 with dilute hydrochloric acid and the solution extracted with hexane to remove the unreacted amino diester. The aqueous solution was adjusted to a pH of 5.3 and was then extracted with diethyl ether. The combined extracts were washed with brine, dried over anhydrous sodium sulfate and concentrated, giving 18.3 g (65%) of the title compound as an oil.

Analysis for: $C_{15}H_{19}NO_4$. Calculated: C, 64.96; H, 6.91; N, 5.05. Found: C, 64.35; H, 6.97; N, 5.04.

EXAMPLE 2

2,5-pyrrolidinecarboxylic acid monoethyl ester

A solution of trans-N-benzyl-2,5-pyrrolidine dicarboxylic acid monoethyl ester (9.0 g, 0.032 m) in ethanol (250 ml) was hydrogenated with 1.5 grams of 10% Pd/C catalyst. The catalyst was filtered off and the filtrate evaporated yielding a solid. The product was recrystallized from ethanol (4.7 g, 80%), m.p. 157°–8° C.

Analysis for: $C_8H_{13}NO_4$. Calculated: C, 51.33; H, 6.99; N, 7.48. Found: C, 51.16; H, 6.89; N, 7.39.

EXAMPLE 3

N-benzyloxycarbonyl-2,5-pyrrolidine dicarboxylic acid monoethyl ester

To an aqueous solution of trans-2,5-pyrrolidine dicarboxylic acid monoethyl ester (4.8 g, 0.25 m) at 5° C. was simultaneously added benzyl chloroformate (4.8 ml, 0.032 m) and a solution of sodium carbonate (5.4 g, 0.05 m) in water (20 ml). The mixture was stirred at 5° C. for 45 minutes and then extracted with ether. The aqueous mixture was acidified to pH 3 with dilute hydrochloric acid and extracted with diethyl ether. The combined extracts were washed with brine, and dried over anhydrous sodium sulfate. The solvent was evaporated to yield the title compound as an oil.

Analysis for: $C_{16}H_{19}NO_6$. Calculated: C, 59.80; H, 5.96; N, 4.36. Found: C, 59.62; H, 6.07; N, 4.37.

EXAMPLE 4

5-ethoxycarbonyl-N-benzyloxycarbonyl-2-[(2'-(S)-benzylcarbonyl)-1'-pyrrolidinylcarbonyl]pyrrolidine Thionyl chloride (20 ml) was slowly added to trans-N-benzyloxycarbonyl-2,5-pyrrolidine dicarboxylic acid monoethyl ester (3.3 g, 0.01 m) and the mixture was refluxed for 3 hours. The thionyl chloride was distilled off giving the acid chloride as an oil.

To a solution of O-benzyl-L-prolinate hydrochloride (2.5 g, 0.01 m) and diisopropylethylamine (4.5 g, 0.025 m) in methylene chloride (60 ml) at 5° C. was slowly added trans-N-benzyloxycarbonyl-2,5-pyrrolidine dicarboxylic acid chloride ethyl ester. The mixture was stirred at room temperature for 2 days. It was then extracted with 10% hydrochloric acid, washed with brine, dried over anhydrous sodium sulfate and the solvent evaporated off to yield the title compound as an oil (4.5 g, 85%).

$[\alpha]_D^{26} = -75.33$ (c=0.98%, EtOH).

Analysis for: $C_{27}H_{32}N_2O_5$. Calculated: C, 66.12; H, 6.34; N, 5.51. Found: C, 66.01; H, 6.27; N, 5.36.

EXAMPLE 5

5-ethoxycarbonyl-2-[(2'-(S)-carboxy)-1'-pyroolidinylcarbonyl]pyrrolidine

A solution of trans-5-ethoxycarbonyl-N-benzyloxycarbonyl-2-[(2'-(S)-benzyloxycarbonyl)-1'-pyrrolidinylcarbonyl]pyrrolidine (2.0 g, 0.0039 m) and triethylamine (0.4 g, 0.0039 m) in ethanol (100 ml) was hydrogenated with 10% Pd/C (0.2 g) catalyst. The catalyst was filtered off and the filtrate was evaporated to an oil. This material was dissolved in water and passed through an ion exchange column (Ag 50$^w$-X8, sodium form). The sodium salt of the title compound was isolated from the chromatographic fractions as a solid, m.p. 90° C. $[\alpha]_D^{24} = -13.37$ (c=0.83%, MeOH).

Analysis for: $C_{13}H_{19}N_2O_5Na$. Calculated: C, 50.97; H, 9.15; N, 6.25. Found: C, 51.30; H, 8.80; N, 6.37.

What is claimed is:

1. A compound of the formula:

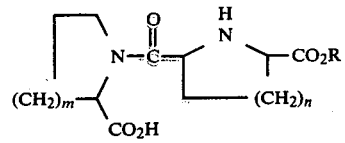

wherein
R is alkyl of 1 to 6 carbon atoms or aralkyl of 7 to 9 carbon atoms, and
m and n are, independently, one of the integers 1 or 2, or a pharmaceutically acceptable salt thereof.

2. A compound of claim 1 of the formula:

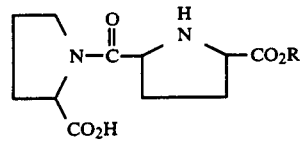

wherein R is alkyl of 1 to 4 carbon atoms; or a pharmaceutically acceptable salt thereof.

3. A compound of claim 2 in which the two derivatized carboxyl groups are in trans configuration.

4. A compound of claim 2 which is 5-ethoxycarbonyl-2-(2'-carboxy-1'-pyrrolidinylcarbonyl)pyrrolidine or a pharmaceutically acceptable salt thereof.

5. The compound of claim 2 which is trans-5-ethoxycarbonyl-2-[(2'-(S)-carboxy)-1'-pyrrolidinylcarbonyl]-pyrrolidine or a pharmaceutically acceptable salt thereof.

6. A compound of the formula:

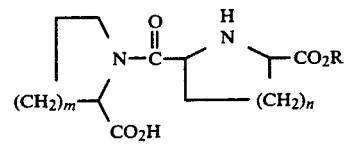

wherein
R is alkyl of 1 to 6 carbon atoms, benzyl, phenethyl or dimethylbenzyl; and
m and n are, independently, one of the integers 1 or 2; or a pharmaceutically acceptable salt thereof.

* * * * *